(12) United States Patent
Heidschmidt et al.

(10) Patent No.: US 11,638,803 B2
(45) Date of Patent: May 2, 2023

(54) ANESTHETIC EVAPORATOR UNIT

(71) Applicant: Drägerwerk AG & Co. KGaA, Lübeck (DE)

(72) Inventors: Michael Heidschmidt, Lübeck (DE); Klaus Radomski, Lübeck (DE); Thomas Lutter, Lübeck (DE); Franz Mair, Munich (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 2248 days.

(21) Appl. No.: 14/959,330

(22) Filed: Dec. 4, 2015

(65) Prior Publication Data

US 2016/0175555 A1   Jun. 23, 2016

(30) Foreign Application Priority Data

Dec. 17, 2014   (DE) .................. 10 2014 018 602.4

(51) Int. Cl.
*A61M 16/18*   (2006.01)
*A61M 16/10*   (2006.01)
(Continued)

(52) U.S. Cl.
CPC ........ *A61M 16/18* (2013.01); *A61M 16/0003* (2014.02); *A61M 16/1075* (2013.01);
(Continued)

(58) Field of Classification Search
CPC ............... A61M 11/042; A61M 16/18; A61M 2205/3368; A61M 11/044; A61M 11/045; A61M 11/048; A61M 16/00; A61M 16/10; A61M 11/041; A61M 16/1045; A61M 16/1075; A61M 16/109; A61M 16/147; A61M 16/16; A61M 16/162; A61M 16/167; A61M 16/168; A61M 2205/3653; F28D 15/0266; F28D 15/0275; F28D 15/046;
(Continued)

(56) References Cited

U.S. PATENT DOCUMENTS

| | | | | |
|---|---|---|---|---|
| 3,540,445 A | * | 11/1970 | Moyat | A61M 16/18 128/204.13 |
| 4,225,542 A | * | 9/1980 | Wall | A61M 16/1075 128/203.12 |
| 4,693,853 A | * | 9/1987 | Falb | A61M 16/186 128/202.27 |
| 5,992,700 A | * | 11/1999 | McGlothlin | A61M 5/1486 222/187 |
| 6,275,650 B1 | | 8/2001 | Lambert | |
| 9,987,456 B2 | * | 6/2018 | Lee | A61M 16/1045 |

(Continued)

FOREIGN PATENT DOCUMENTS

| CN | 101112673 A | 1/2008 |
|---|---|---|
| CN | 101239214 A | 8/2008 |

(Continued)

*Primary Examiner* — Justine R Yu
*Assistant Examiner* — Matthew R Moon
(74) *Attorney, Agent, or Firm* — McGlew and Tuttle, P.C.

(57) ABSTRACT

An anesthetic evaporator unit (2) with an anesthetic container (4) for receiving liquid anesthetic, with a gas line (6) with an open-pore, porous line wall (8) for guiding gas and for enriching the gas with anesthetic, and with an anesthetic-guiding wick (10), which extends from an interior space (12) of the anesthetic container (4) to the line wall (8) in order to supply the line wall (8) with anesthetic from the anesthetic container (4). The anesthetic evaporator unit (2) has a heater (14) for heating the gas line (6). A method for controlling the anesthetic evaporator unit (2) is also provided.

2 Claims, 3 Drawing Sheets

(51) Int. Cl.
  *A61M 16/00* (2006.01)
  *A61M 16/14* (2006.01)
  *A61M 16/08* (2006.01)

(52) U.S. Cl.
  CPC ...... *A61M 16/1095* (2014.02); *A61M 16/142* (2014.02); *A61M 16/0875* (2013.01); *A61M 2016/1035* (2013.01); *A61M 2205/3334* (2013.01); *A61M 2205/3368* (2013.01); *A61M 2205/3653* (2013.01)

(58) Field of Classification Search
  CPC ............... A01M 1/2033; A01M 1/2044; A61L 9/122; A61L 9/127; B01B 1/005; B01F 11/30; F24F 11/30; F24F 2110/00; F24F 6/043; F24F 6/08; F24F 6/10; F24H 1/00; Y10S 165/398; Y10S 165/907; Y10S 261/34; Y10S 261/65; Y10T 137/7358; Y10T 29/49861; Y10T 428/24314
  See application file for complete search history.

(56) References Cited

U.S. PATENT DOCUMENTS

| | | | |
|---|---|---|---|
| 2005/0133030 A1* | 6/2005 | Fiedorowicz | A61M 16/18 128/204.13 |
| 2011/0146679 A1* | 6/2011 | Heesch | A61M 16/209 128/204.17 |
| 2013/0220314 A1* | 8/2013 | Bottom | A61M 16/0891 128/200.14 |
| 2015/0020803 A1* | 1/2015 | Dunlop | A61M 16/0875 128/203.14 |

FOREIGN PATENT DOCUMENTS

| | | |
|---|---|---|
| DE | 10 2005 000 690 B3 | 5/2006 |
| DE | 10 2005 005 349 B3 | 6/2006 |
| DE | 10 2005 054 344 B3 | 6/2007 |
| DE | 10 2008 045 081 A1 | 3/2010 |
| GB | 2279015 A | 12/1994 |
| WO | 2008095245 A1 | 8/2008 |

* cited by examiner

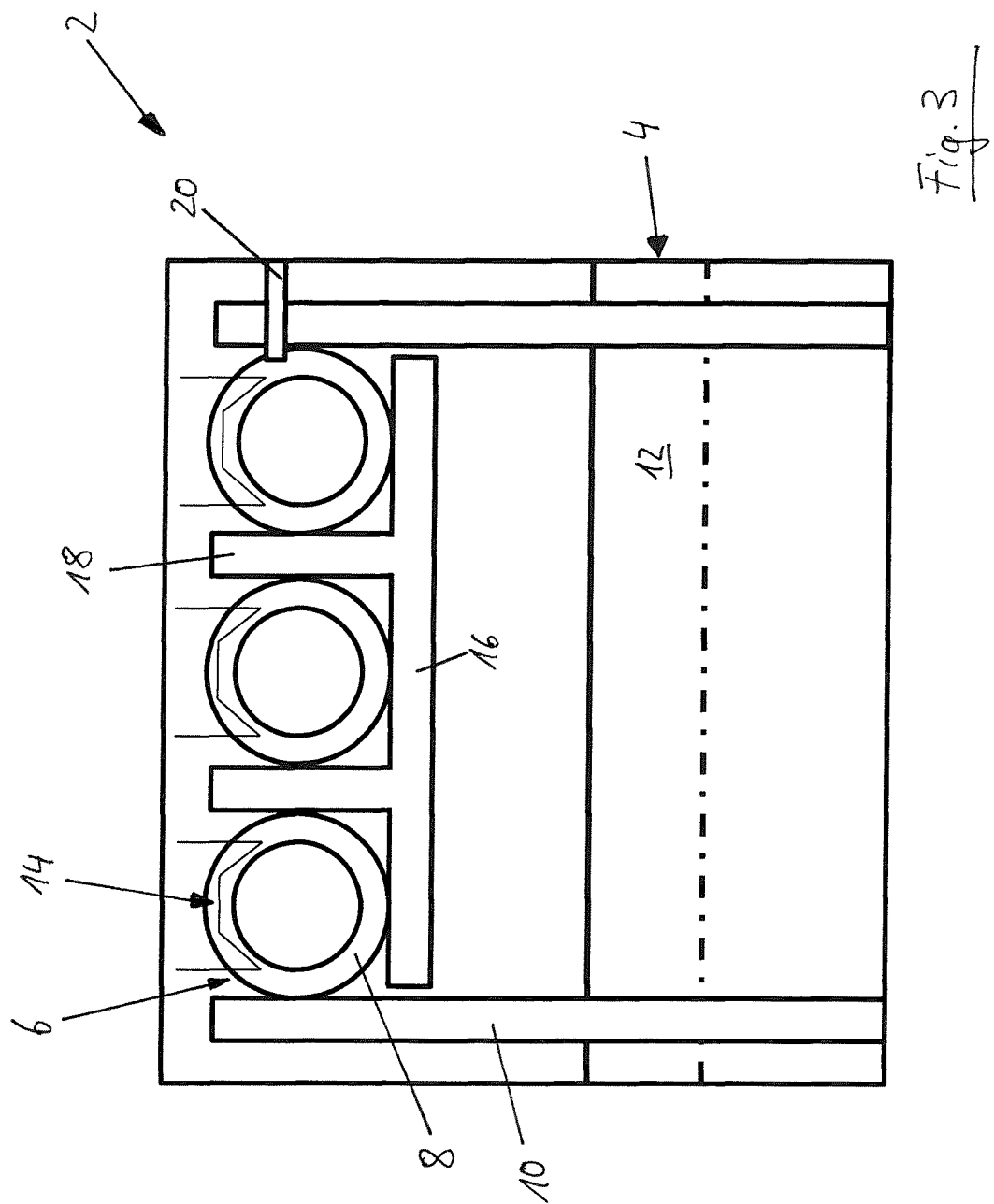

ANESTHETIC EVAPORATOR UNIT

CROSS REFERENCE TO RELATED APPLICATIONS

This application claims the benefit of priority under 35 U.S.C. § 119 of German Patent Application 10 2014 018 602.4 filed Dec. 17, 2014, the entire contents of which are incorporated herein by reference.

FIELD OF THE INVENTION

The present invention pertains to an anesthetic evaporator unit with an anesthetic container for receiving liquid anesthetic, with a gas line with an open pore, porous line wall for guiding gas and for enriching the gas with anesthetic, and with an anesthetic-guiding wick, which extends from an interior space of the anesthetic container to the line wall, in order to supply the line wall with anesthetic from the anesthetic container.

BACKGROUND OF THE INVENTION

Such anesthetic evaporator units are known, in principle, from the state of the art. Anesthetic evaporator units are used to enrich a gas, which is preferably also called carrier gas, with a volatile anesthetic. The volatile anesthetic is stored for this in an anesthetic container of the anesthetic evaporator unit. To release the anesthetic to a gas, which flows through a gas line of the anesthetic evaporator unit, the line wall of the gas line is porous with open pores. Consequently, the liquid anesthetic can be absorbed from the line wall by means of capillary forces, stored and released. The release takes place preferably into the inner duct, which is formed by the gas line. The gas or carrier gas, which becomes enriched with the anesthetic evaporating during the release due to the release of the anesthetic from the pores of the line wall, flows here. The length of the gas line is preferably selected to be such that a desired enrichment of the gas with anesthetic is achieved. Even though the gas line with the corresponding, open pore, porous line wall can absorb, store and release the anesthetic towards the radial inner side, the gas line is not intended for use as a primary storage means for the liquid anesthetic. The anesthetic container is used for this purpose. To always supply the gas line or the corresponding line wall with a sufficient quantity of anesthetic, an anesthetic-guiding wick is provided. The wick is, for example, a wick consisting of a fabric material. As an alternative or in addition, a porous, preferably open-pore solid wick may be provided. Such a solid wick preferably consists of a porous sintered metal or a porous sintered ceramic. As an alternative, the solid wick may also be manufactured from a porous, open-pore plastic. This also applies to the line wall of the gas line. Due to the wick extending from an interior space of the anesthetic container to the line wall, the liquid anesthetic can be transported from the anesthetic container to the line wall by means of capillary forces. The wick is consequently used to supply the line wall with anesthetic from the anesthetic container.

To enrich a gas flowing through the gas line with anesthetic, the anesthetic must evaporate on the boundary surface from the line wall to the gas. The anesthetic is suitable for this, in principle, because the anesthetic is preferably a volatile anesthetic. However, a corresponding power or energy is needed for the evaporation of the anesthetic. The evaporation energy or evaporation output necessary for the evaporation of the liquid anesthetic is made available in conventional anesthetic evaporator units by means of heat conduction from a usually metallic part of the anesthetic evaporator unit. In other words, a certain heat flux, which is proportional to the specific thermal capacity of said metallic part, to the mass of the metallic part and to the temperature difference of the metallic part during cooling, must be made available for the desired evaporation of the anesthetic. Since the specific heat capacity of the metallic part is constant and only a limited, often small temperature difference can usually be reached, the mass of the metallic part must be adapted to the necessary evaporation output, because there is otherwise a risk that cooling of the metallic part is associated with the evaporation, and no energy transport is possible any more for the evaporation beginning from a certain temperature limit of the metallic part. To avoid this, such a metallic part is provided with a mass of several kg in conventional anesthetic evaporator units, which makes the handling of a corresponding anesthetic evaporator unit appreciably more difficult. In addition, the material costs of the metallic part make a considerable contribution.

SUMMARY OF THE INVENTION

A basic object of the present invention is consequently to provide an anesthetic evaporator unit that can be handled in an especially simple manner and can be manufactured under favorable conditions.

According to the invention, an anesthetic evaporator unit is provided with an anesthetic container for receiving liquid anesthetic, with a gas line with an open pore, porous line wall for guiding gas and for enriching the gas with anesthetic, and with an anesthetic-carrying wick, which extends from an interior space of the anesthetic container to the line wall in order to supply the line wall with anesthetic from the anesthetic container, wherein the anesthetic evaporator unit has a heater for heating the gas line.

As can be determined from the above, the transition of the liquid phase of the anesthetic to the gaseous phase takes place at the transition of the line wall to the gas flowing through the gas line. The evaporation energy or output necessary for the corresponding evaporation is provided according to the present invention by the heater. This is used to heat the gas line and can therefore feed the energy directly at the site at which the corresponding evaporation of the anesthetic, which was explained above, takes place. Therefore, the evaporation energy or output necessary for the evaporation is not taken from a large and heavy metal part, since this is guaranteed, according to the invention, by the heater. A corresponding metallic part may therefore be made markedly smaller. It may also be possible to do away with the metallic part altogether. To ensure the highest possible efficiency of the energy added through the heater and of the evaporation energy necessary for the evaporation, the heat radiation of the heater is directed in the direction of the gas line and the corresponding line wall. The heater may consequently have a preferred direction, in which the heat provided by the heater is radiated. This preferred direction points in the direction of the gas line and the line wall. Such a heater may be a heater known from the state of the art. In particular, the heater may be an electric heater. The heater may therefore have an especially low weight. Moreover, the heater can be manufactured with an especially small space requirement. An anesthetic evaporator unit with the heater according to the present invention can therefore be manufactured as an especially small or compact unit and with a low weight. This facilitates the handling. In addition, the manufacturing costs decrease.

A preferred embodiment of the anesthetic evaporator unit is characterized in that the heater is a gas line heater. The heater can consequently be configured specifically and especially for supplying a gas line or the corresponding line wall with heat. This increases the efficiency in the transmission of heat from the heater to the gas line and to the corresponding line wall. The heater can thus be made more compact and possibly designed with a lower output because of its higher efficiency. This reduces both the manufacturing costs and the space needed for the heater in the anesthetic evaporator unit, which leads to a further improvement in the ease of handling.

Another advantageous embodiment of the anesthetic evaporator unit is characterized in that the heater is an electric heater. An electric heater for the anesthetic evaporator unit has proved to be especially advantageous in practice, because it has an especially low inertia in time. The heater can thus be controlled especially simply and quickly in order to transmit the particular quantity of heat necessary to the gas line or the corresponding line wall. In other words, it can be achieved with an electric heater in an especially simple manner that the amount of heat transmitted from the heater to the gas line or to the corresponding line wall is not too large and not too small.

Another advantageous embodiment of the anesthetic evaporator unit is characterized in that the gas line is held by a holder, with which the heater is associated. The gas line is provided with an open pore, porous line wall. The line wall may consequently be formed by a textile. It is possible, as an alternative, that the line wall is formed by an open pore, porous metal, plastic or ceramic material. It common to all embodiments of the line wall that they often have a low dimensional stability. To place the gas line at the desired location in the anesthetic evaporator unit, the holder may be provided, which is configured to hold the gas line. The holder may consequently have direct contact with the gas line. Due to the heater being associated with the holder, an especially tight arrangement of the heater in relation to the gas line or to the corresponding line wall can be guaranteed. In particular, the heater may form part of the holder, so that the space needed for installation is not large or at least no additional space is essentially required. It is advantageous, in principle, but especially in reference to the holder, if the heater has direct contact with the gas line or the line wall. In case the heater forms part of the holder, the contact between the heater and the gas line or the corresponding line wall can be established in an especially simple and reliable manner. The heater may be configured in this case corresponding to an outer contour of the line wall. In addition, it proved to be advantageous if the holder is configured for heat conduction. Thus, the holder may be, for example, a metallic holder. The holder can thus be used to distribute the heat released by the heater in order to supply the line wall with the heat of the heater over the longest possible section. Consequently, the heat can be transmitted not only in a punctiform manner over a small section of the area to the line wall, but it can be transmitted over a large surface to the line wall by means of the especially good thermal conductivity of the holder. This improves the evaporation of the anesthetic, so that the length of the gas line can be kept especially short. The compactness of the anesthetic evaporator unit can be further improved with the especially short length of the gas line.

Another advantageous embodiment of the anesthetic evaporator unit is characterized in that the heater is at least partially integrated in the line wall. The heater can thus be placed even closer to the location at which the phase transition from the liquid anesthetic to the gaseous anesthetic takes place, because, due to the integration of the heater into the line wall, the heater is located only at a short distance from the radially inner wall surface of the line wall, at which the evaporation takes place at least essentially. The heat can consequently be supplied in a specific manner with the integration of the heater into the line wall. This facilitates the controllability of the output or energy necessary for the evaporation. Moreover, the dimensional stability of the gas line can be increased with the integration of the heater, so that a smaller holder can be used to hold the gas line. In particular, the holder can be eliminated altogether in case of an especially dimensionally stable design of the heater. The space requirement can therefore be reduced with the integration of the heater in the line wall, which leads to a further increase in the compactness of the anesthetic evaporator unit. In case no holder is needed, the weight of the anesthetic evaporator unit also decreases appreciably, so that, moreover, the ease of handling of the anesthetic evaporator unit is improved.

Another advantageous embodiment of the anesthetic evaporator unit is characterized in that the heater has lamellae (radiator ribs/heat transfer fins), which are arranged on the outside adjacent to and in contact with the line wall of the gas line. It was found in practice that a heater with a higher heat output is necessary for certain anesthetics. To transmit this heat output to the gas line or to the corresponding line wall, it proved to be advantageous to provide the aforementioned radiator ribs for the heater. Such radiator ribs are configured for heat transmission. They can consequently transmit the heat to be released from a heat source of the heater to the gas line or to the corresponding gas line wall. Due to their direct contact with the line wall, a heat loss is, moreover, reduced or avoided. The heat supply by means of the heater to the line wall can be controlled especially accurately with the especially low heat loss. If the gas line is arranged in loops and/or rings, the radiator ribs may extend between adjacent sections of the gas line, so that an assembly unit of the gas line and the heater can be configured as an especially compact unit. This reduces the necessary volume for the installation of the anesthetic evaporator unit, which improves the ease of handling of the anesthetic evaporator unit.

Another advantageous embodiment of the anesthetic evaporator unit is characterized in that the wick is configured as a textile wick. The corresponding textile may have a plurality of fibers in order to form the wick. Spaces or hollow chambers defined by the fibers, which may be called pores because of their usually small size, may be formed between the fibers. The pores may absorb liquid anesthetic. In addition, the pores may be in fluid connection with one another in order to make possible the exchange and/or transportation of anesthetic. The pores are not closed by the fibers on the outside. One may therefore also speak of open pores. In other words, the textile wick may be an open-pore wick on the outside.

Another advantageous embodiment of the anesthetic evaporator unit is characterized in that the gas line is configured as a textile gas line. Concerning the advantageous features and effects of the textile for the gas line, reference is made analogously to the above explanation. The textile for the gas line may thus likewise have fibers, which form pores for absorbing liquid anesthetic. The textile gas line is therefore configured for the transportation of liquid anesthetic with the fibers or the pores. In addition, the fibers or the pores may be configured such as to have open pores on the outer side of the gas line in at least some sections in order to make possible the transition of the anesthetic to the carrier gas.

Another advantageous embodiment of the anesthetic evaporator unit is characterized in that the gas line and the wick are made integrally. They can consequently form an integral unit. This facilitates the transportation of the liquid anesthetic from the interior space of the anesthetic container to the line wall. In other words, the resistance to the transportation of the liquid anesthetic, which is pressed by means of capillary forces from the anesthetic container to the radially inner surface of the line wall, is reduced. A larger quantity of liquid anesthetic can be transported with the reduced resistance from the interior space of the anesthetic container to the line wall in a comparable time. This larger quantity of anesthetic can be evaporated by the heater according to the present invention and released to the gas flowing through the gas line, since the heat output of the heater can set and controlled. Consequently, there is no unintended interruption in the evaporation of the anesthetic. In summary, the anesthetic can be transmitted to the gas flowing through the gas line over a shorter section of the gas line with the heater and due to the integral design of the wick and the gas line. It is thus possible to make the gas line shorter, which in turn improves the compactness and the ease of handling of the anesthetic evaporator unit.

Another advantageous embodiment of the anesthetic evaporator unit is characterized in that a temperature sensor is provided for detecting a temperature of the gas in the gas line. Based on the temperature of the gas flowing through the gas line, the saturation concentration with anesthetic can be determined. The temperature sensor may therefore be advantageously used to control the anesthetic evaporator unit and especially the heater. If, for example, a higher concentration of anesthetic is desired in the gas flowing through the gas line, the temperature sensor can provide information on whether this concentration can, in principle, be reached and if so, how the heater is to be controlled to guarantee a corresponding evaporation of the anesthetic and hence a transfer of the anesthetic to the gas.

Another advantageous embodiment of the anesthetic evaporator unit is characterized in that a temperature sensor is provided for detecting a temperature representing the temperature of the gas flowing through the gas line. The temperature sensor can thus measure, for example, the temperature of the line wall, of the holder and/or of another adjacent device in order to infer the temperature of the gas at least approximately or at least essentially on the basis of this measured temperature. Improved control of the heater and/or other analyses, as they were explained above, can be performed with this temperature representing the gas temperature analogously to the measured gas temperature. This improves the quality of enrichment of the gas flowing through the gas line with anesthetic, and a more accurate concentration of the anesthetic can be set in the gas flowing through the gas line.

According to another aspect, the object described in the introduction is accomplished by a method for controlling the anesthetic evaporator according to the present invention, wherein the output of the heater is controlled as a function of a gas flow through the gas line, the temperature detected by means of the temperature sensor and/or an anesthetic concentration in the gas flowing through the gas line. The basic idea of this aspect of the present invention is that the gas line or the line wall must also be supplied with a larger quantity of anesthetic per unit of time in case of a larger gas flow in order to reach the desired anesthetic concentration in the gas flowing through the gas line. A flow sensor, which can detect the gas flow of a gas through the gas line, may be provided for this purpose for the anesthetic evaporator unit. The sensor may be a volume flow sensor and/or a mass flow sensor. Sensors that measure values representing the above-mentioned values shall also be detected in the process. The temperature of the gas flowing through the gas line is, moreover, decisive for the maximum concentration of anesthetic in the gas flowing through the gas line. It can consequently be determined with this temperature how much anesthetic can be transferred to the gas flowing through the gas line. In addition, the heat output can be limited with the measured temperature of the gas in order to prevent anesthetic from precipitating in a duct area, which adjoins an outlet of the gas line. Consequently, especially reliable operation of the anesthetic evaporator unit can be guaranteed with the detection of the temperature of the gas in the gas line. With the detection of the anesthetic concentration in the gas flowing through the gas line, especially at an outlet of the gas line, it is possible to guarantee that reliable information will be obtained on whether the desired anesthetic concentration is reached or not. Should the anesthetic concentration not have been reached, a corresponding regulation may be provided for the anesthetic evaporator unit in order to increase or decrease the evaporation of the anesthetic by the regulation increasing or decreasing the heat output. In other words, the heat of the heater can be regulated by detecting the anesthetic concentration and a comparison with a designed anesthetic concentration. With such a design, the anesthetic evaporator unit can always provide the desired anesthetic concentration in the gas flowing out of the gas line, which permits especially reliable anesthesia.

The present invention will be explained in more detail below on the basis of exemplary embodiments with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is schematic cross-sectional view of a third embodiment of the anesthetic evaporator unit.

DESCRIPTION OF THE PREFERRED EMBODIMENTS

Figure 1:
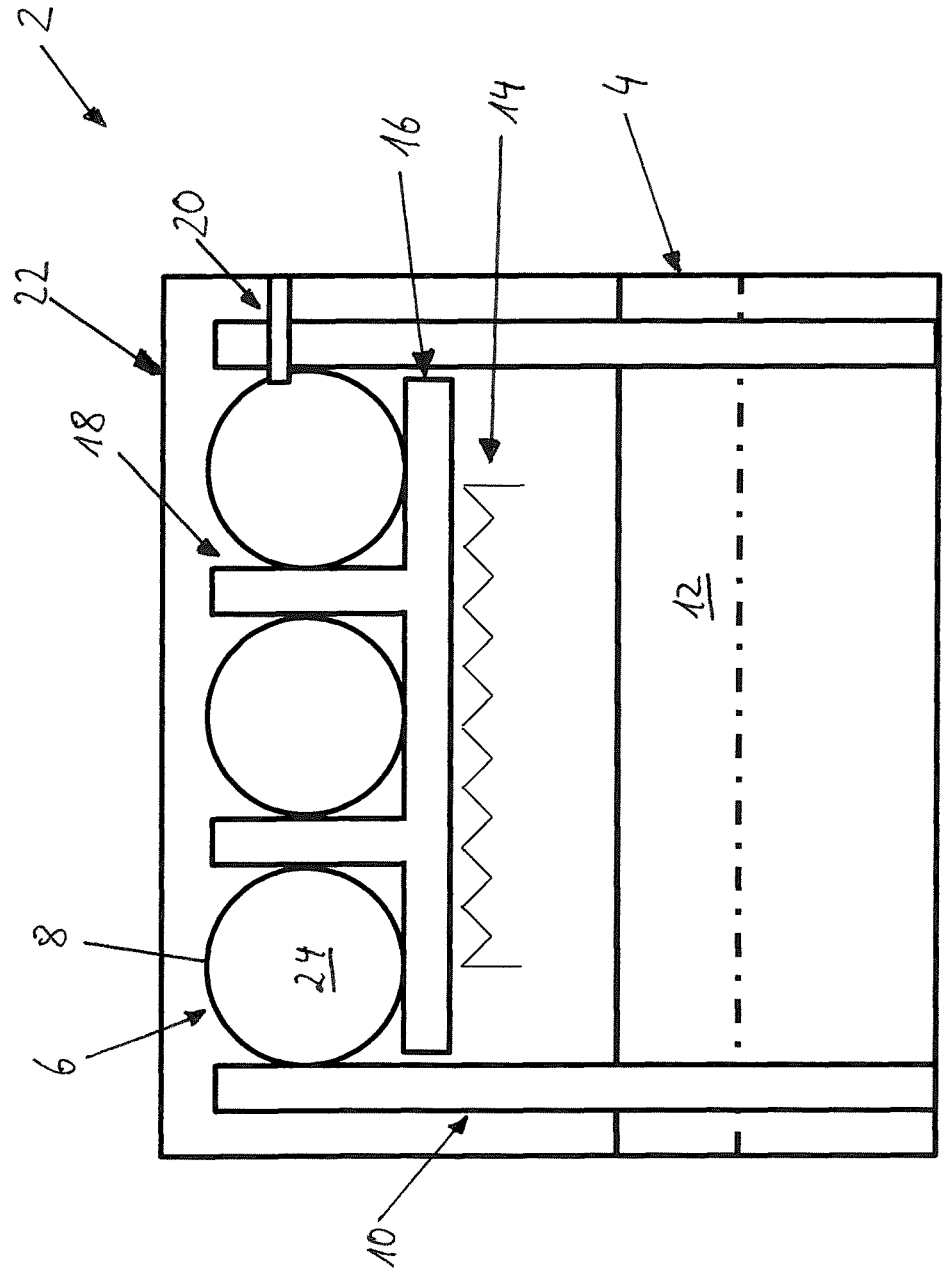
FIG. 1 is a schematic sectional view of a first embodiment of an anesthetic evaporator unit.

Referring to the drawings, FIG. 1 schematically shows the anesthetic evaporator unit 2 according to the present invention in a cross-sectional view. The anesthetic container 4 is arranged at a anesthetic evaporator unit bottom. The anesthetic container 4 is used to receive liquid anesthetic. A closure, with which the liquid anesthetic can be filled into the interior space 12 of the anesthetic container 4, may be provided for this. The broken (phantom) line in FIG. 1 designates a fill level, the anesthetic container 4 shown in FIG. 1 is filled with liquid anesthetic to about half. The evaporation assembly unit 22 of the anesthetic evaporator assembly unit 2 adjoins above the anesthetic container 4. The evaporation assembly unit 22 comprises a housing, which is connected to and/or is made integrally in one piece with the anesthetic container 4. The gas line 6, which is configured to guide gas, passes through or in the housing of the evaporation assembly unit 22. Carrier gas flows into the gas line 6 at an inlet of the gas line 6 in order to subsequently become enriched with anesthetic during its flow through the gas line 6. The gas line 6 has an open-pore, porous line wall 8 for this. Therefore, the carrier gas enriched with anesthetic follows out of the gas line 6 at the end of the gas line 6. This carrier gas enriched with anesthetic can then be used to anesthetize a person. A wick 10 is provided to transport the anesthetic from the anesthetic container 4 to the gas line 6. The wick 10 is configured to guide or transport liquid anesthetic. Such a wick 10 is configured, for example, as a textile wick or as a porous plastic, ceramic or metal wick that has open pores in at least some sections. The wick 10 is consequently suitable for guiding anesthetic by means of capillary force from the interior space 12 of the anesthetic container 4 to the gas line 6. The wick 10 extends correspondingly from this, namely, from an interior space 12 of the anesthetic container 4 to the gas line 6. The wick 10 is directly contacted with the gas line 6 or is configured as an integral component. Consequently, the line wall 8 of the gas line 6 can be sufficiently supplied with liquid anesthetic through the wick 10. If carrier gas is flowing in this case through the gas line 6, anesthetic evaporates from the pores of the line wall 8 into the surrounding duct space 24 of the gas line 6, so that the gas flowing through the gas line 6 is enriched with anesthetic. To guarantee continuous evaporation during the flow of gas through the gas line 6, the gas line 6 is to be supplied with energy, preferably with thermal energy, since the evaporation would otherwise deteriorate, so that a smaller quantity of anesthetic would be transferred to the gas flowing through, which is to be avoided. To transfer the desired or necessary quantity of anesthetic from the line wall 8 of the gas line 6 to the gas flowing through the gas line 6, the heater 14, which is configured to heat the gas line 6, is provided according to the present invention.

As can be seen from FIG. 1, the heater 14 is located directly adjacent to and preferably in contact with a holder 16, which is configured to hold the gas line 6. The holder 16 has a high coefficient of thermal conduction, so that it can absorb the heat released by the heater 14 and release it to the gas line 6 especially well. The holder 16 may be in direct contact with the gas line 6 for this purpose. This guarantees an especially good heat transfer from the heater 14 via the holder 16 to the gas line 6. In summary, it can consequently be stated that the heater 14 is configured as a gas line heater, because there is a direct contact between the heater 14 and the gas line 6 and/or a heat-conducting holder 16 is provided in-between for heat transfer and/or heat distribution.

As can be determined from FIG. 1, the gas line 6 may be arranged next to each other in some sections. This is the case, for example, when the gas line 6 is arranged in a meandering or helical pattern. It proved to be advantageous in this case if the heater 14 and/or the holder 16 has/have heat radiator ribs (lamellae) 18, which extend between line sections of the gas line 6. The radiator ribs 18 are therefore adjacent from the outside and in contact with the gas line wall 8 of the gas line 6. This guarantees especially good transfer of the heat released by the heater 14 to the line wall 8 of the gas line 6.

Figure 2:
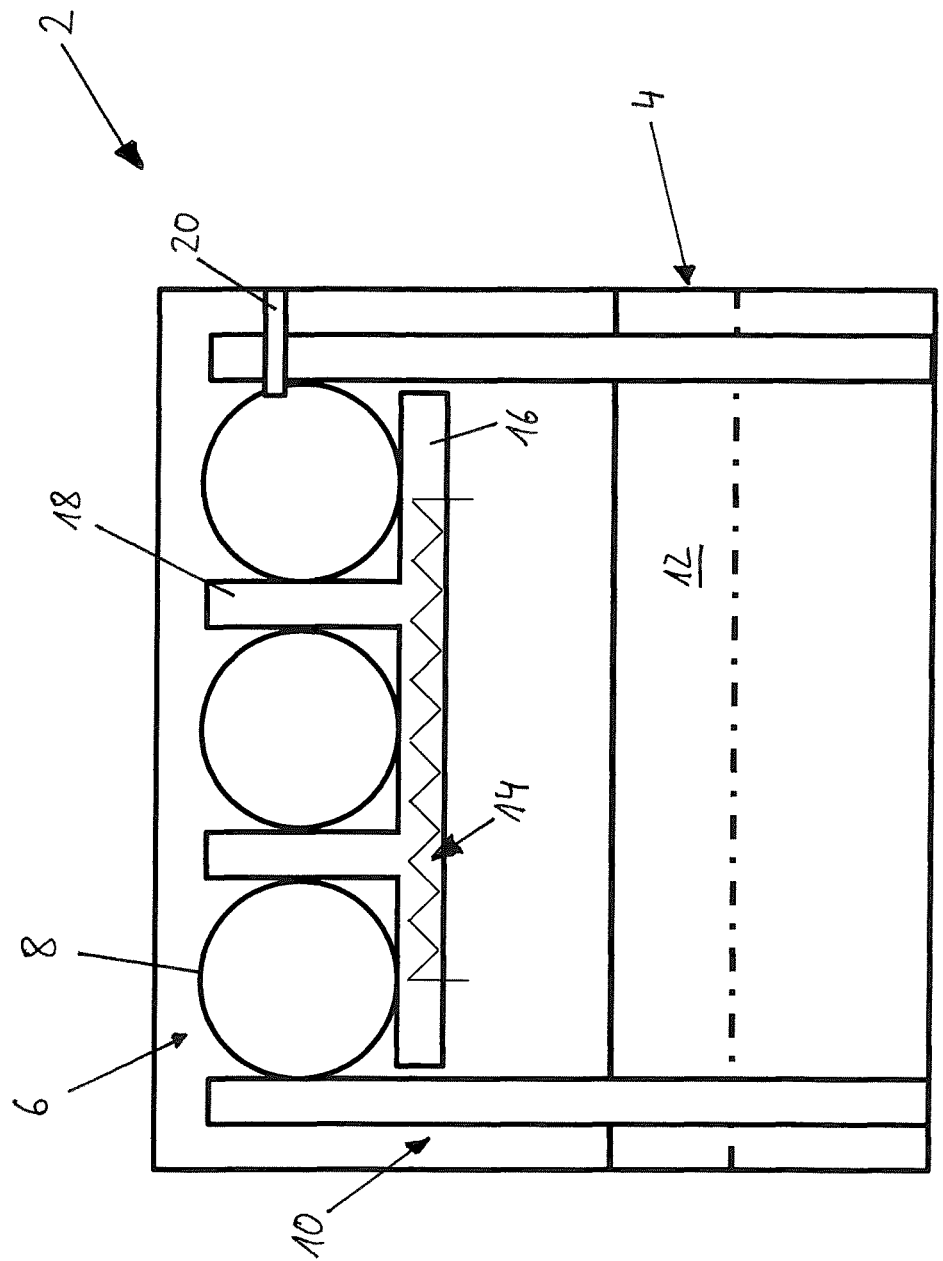
FIG. 2 is a schematic sectional view of a second embodiment of an anesthetic evaporator unit.

FIG. 2 shows another embodiment of the anesthetic evaporator unit 2 according to the present invention. The basic design of the anesthetic evaporator unit 2 from FIG. 2 is identical to that of the anesthetic evaporator unit 2 from FIG. 1. Reference is therefore analogously made to the explanations given above insofar as doing so is meaningful. A difference of this embodiment of the anesthetic evaporator unit 2 from FIG. 2 can be seen in the arrangement of the heater 14. The heater 14 is associated with the holder 16. The heater 14 is integrated in the holder 16. The holder 16 is preferably configured as a metallic holder 16. The holder 16 thus has a high coefficient of thermal conduction and is especially well suited for transporting and distributing the heat released by the heater 14 to the line wall 8 of the gas line 6. The heat radiator ribs 18 are likewise formed by the holder 16, so that the line wall 8 of the gas line 6 is contacted by the holder 16 at at least a plurality of locations over the circumference of the ring, so that the most uniform distribution possible of the heat supply is guaranteed. The liquid anesthetic absorbed by the line wall 8 of the gas line 6, which is located in the pores, can be heated by the heat supply, so that evaporation and hence transfer of the anesthetic to the gas flowing through the gas line 6 is facilitated. In addition, it can be guaranteed by the continuous supply of heat by means of the heater 14 that the transfer of the anesthetic from the pores of the line wall 8 to the gas flowing through the gas line 6 will also take place continuously, and preferably as desired.

A temperature sensor 20 may be provided to enrich the gas flowing through the gas line 6 with the desired quantity of anesthetic at the outlet of the gas line 6 or to reach the desired anesthetic concentration. The temperature sensor 20 is preferably arranged at an outlet section of the gas line 6. As an alternative, the temperature sensor 20 may also be arranged at another section of the gas line 6. The temperature of the gas flowing through the gas line 6 can be detected with the temperature sensor 20. The temperature sensor 20 may be integrated for this purpose in the line wall 8 and/or it may protrude into the duct space 24 formed by the gas line 6. How much anesthetic can be fed to the gas flowing through the gas line 6 can be determined with the detected temperature of the gas flowing through the gas line 6. In other words, the maximum anesthetic concentration can be determined. If the maximum anesthetic concentration has not yet been reached in the gas flowing through the gas line 6, the temperature of the heater 14 can be correspondingly increased in order to increase the particular current anesthetic concentration in the gas flowing through the gas line 6. As an alternative or in addition, the gas flow through the gas line 6 can be detected in order to control the heat output of the heater 14. It proved to be advantageous in practice if, moreover, a regulation is provided, with which the anesthetic concentration in the gas flowing out of the gas line 6 can be regulated. Thus, a sensor can, moreover, be provided for detecting the anesthetic concentration in the gas flowing out of the gas line 6, the detected value being used to set the output of the heater 14. Usual regulation algorithms can be taken into account and/or used in this connection.

FIG. 3 shows another embodiment of the anesthetic evaporator unit 2 according to the present invention. If meaningful, reference is made to the explanations given above in connection with FIGS. 1 and 2 here as well, the anesthetic evaporator unit 2 from FIG. 3 differing due to the arrangement of the heater 14, because the heater 14 is integrated in the line wall 8 of the gas line 6 for this embodiment. The heater 14 may be, for example, an electric wire heater. The electric wire of the heater 14 may be inserted for this purpose into the line wall 8 of the gas line 6 in a meandering, annular or another suitable pattern. This embodiment has proved to be especially energy-efficient, because the heat produced by the heater 14 is directly transmitted to the gas line 6 and to the anesthetic located in the pores of the line wall 8. Thus, there are hardly any losses due to heat transfer. In addition, such a design can be controlled especially well, because there is hardly any time delay between the time at which the heat is released from the heater 14 and the time at which the corresponding heat is absorbed by the line wall 8 or the anesthetic absorbed by the line wall 8. The anesthetic evaporator unit 2 can therefore be controlled and regulated especially accurately and dynamically with correspondingly short time delays.

While specific embodiments of the invention have been shown and described in detail to illustrate the application of the principles of the invention, it will be understood that the invention may be embodied otherwise without departing from such principles.

APPENDIX

List of Reference Numbers

2 Anesthetic evaporator unit
4 Anesthetic container
6 Gas line
8 Line wall
10 Wick
12 Interior space
14 Heater
16 Holder
18 Radiator ribs
20 Temperature sensor
22 Evaporation assembly unit
24 Duct space

What is claimed is:

1. A volatile anesthetic evaporator unit comprising:
an anesthetic container with an interior space with a lower volatile liquid anesthetic region and defining a space above the lower volatile liquid anesthetic region;
an integral component comprising a gas line portion and an anesthetic-guiding wick portion, the gas line portion having an open-pore region defined by a porous line wall, the gas line portion being supported at a position in the space above the lower volatile liquid anesthetic region and spaced from volatile liquid anesthetic in the lower volatile liquid anesthetic region of the anesthetic container, the anesthetic-guiding wick portion extending from the lower volatile liquid anesthetic region of the anesthetic container to the porous line wall and moving the volatile liquid anesthetic from the lower volatile liquid anesthetic region to the space above the lower volatile liquid anesthetic region and at or adjacent to the porous line wall to supply the porous line wall with the volatile liquid anesthetic from the anesthetic container;
an electric heater radiating heat and directing heat radiation of the heater toward the porous line wall to heat the gas line; and
a sensor for sensing at least one of a gas flowing through the gas line, a temperature of gas flowing through the gas line and an anesthetic concentration in the gas flowing through the gas line, wherein the heater is connected to the sensor for controlling a radiated heat output of the heater as a function of at least one of a gas flowing through the gas line, a detected temperature and an anesthetic concentration in the gas flowing through the gas line.

2. An anesthetic evaporator unit in accordance with claim 1, wherein the anesthetic container comprises a reservoir of the anesthetic, wherein one of:
the heater is located between the porous gas line and the reservoir of the anesthetic; and
the heater is located at a position above a holder, wherein the heater is one of:
at least partially integrated in the line wall;
at least partially integrated into a line wall holder with which the heater is associated, wherein the gas line is held by the holder; and
comprised of radiator ribs arranged adjacent to or in contact with an outside of the porous line wall of the gas line.

\* \* \* \* \*